(12) United States Patent
Martorell et al.

(10) Patent No.: US 7,617,615 B1
(45) Date of Patent: Nov. 17, 2009

(54) BELT OR BAND-LIKE EXERCISE RESULT MEASUREMENT ARTICLE WITH SELECTABLE DISPLAY ASPECT

(76) Inventors: Jonathan Martorell, 1401 S. Federal Hwy., No. 416, Boca Raton, FL (US) 33432; Silvina Marcela Gauna, 1401 S. Federal Hwy., No. 416, Boca Raton, FL (US) 33432

( * ) Notice: Subject to any disclaimer, the term of this patent is extended or adjusted under 35 U.S.C. 154(b) by 0 days.

(21) Appl. No.: 12/156,629

(22) Filed: Jun. 3, 2008

(51) Int. Cl.
*G01B 3/10* (2006.01)
*A61B 5/103* (2006.01)

(52) U.S. Cl. .......................................... 33/759; 33/511

(58) Field of Classification Search ................. 33/759, 33/2 R, 755, 776, 555.1, 555.4, 561.1, 561.2, 33/771, 511–512, 11, 16
See application file for complete search history.

(56) References Cited

U.S. PATENT DOCUMENTS

| | | | | |
|---|---|---|---|---|
| 2,428,980 | A * | 10/1947 | McCann | 33/514.2 |
| 4,211,011 | A * | 7/1980 | Jacobson | 33/15 |
| 4,441,258 | A * | 4/1984 | McDaniel et al. | 33/203.11 |
| 4,473,949 | A * | 10/1984 | Schechtman | 33/512 |
| 4,632,393 | A | 12/1986 | Van Noord | |
| 4,868,990 | A * | 9/1989 | Steinberg | 33/15 |
| 5,406,715 | A * | 4/1995 | Koizumi et al. | 33/706 |
| 5,414,943 | A * | 5/1995 | Vogt | 33/764 |
| 5,474,083 | A | 12/1995 | Church | |
| 5,732,475 | A * | 3/1998 | Sacks et al. | 33/555.4 |
| 5,774,999 | A * | 7/1998 | Smith | 33/555.4 |
| 6,401,350 | B2 * | 6/2002 | Ford | 33/562 |
| 6,640,460 | B1 * | 11/2003 | Nabarro et al. | 33/759 |
| 6,725,865 | B2 * | 4/2004 | Chapman | 128/869 |
| 7,111,409 | B2 * | 9/2006 | Janssen | 33/555.4 |
| D536,030 | S | 1/2007 | Wolff et al. | |
| 7,249,423 | B2 * | 7/2007 | Sieber | 33/512 |
| 7,334,472 | B2 | 2/2008 | Seo et al. | |

FOREIGN PATENT DOCUMENTS

| EP | 1074279 A1 | 4/1999 |
|---|---|---|
| EP | 19990917188 | 2/2001 |

OTHER PUBLICATIONS www.portablesupplements.com/mayotape.asp.

* cited by examiner

*Primary Examiner*—Yaritza Guadalupe-McCall
(74) *Attorney, Agent, or Firm*—Melvin K. Silverman; Yi Li

(57) ABSTRACT

A band-like exercise result measurement article with selectable display aspect includes a planar strip of a flexible material having first and second ends, an elastic inner surface and an outer surface of a loop material, the outer surface having, along its length, at least one linear scale imprinted upon it. The article also includes a buckle, a first segment of a hook material affixed to the inner surface near the second end and a second segment of a hook material affixed to the outer surface of the strip near its second end. When the first hook segment is fastened to the outer surface through the buckle, the article displays a measurement of scale. When the second hook segment is fastened to the outer surface through the buckle, the measurement is precluded from display.

10 Claims, 5 Drawing Sheets

BELT OR BAND-LIKE EXERCISE RESULT MEASUREMENT ARTICLE WITH SELECTABLE DISPLAY ASPECT

FIELD OF INVENTION

The present invention relates to exercise belts or bands for use upon the waist or limbs of the human body during exercise, to provide a selectable display of measurement or dimension of the area of interest.

PRIOR ART

Various lifting, training and related exercise devices and systems exist in the prior art. Some or these provide means for measurement of progress during the exercise process. Most however involve the use or electrical or electronic components as, for example, is reflected in U.S. Pat. No. 5,474,083 (1995) to Church, entitled Lifting, Monitoring and Exercise Training System. Other U.S. utility patents also encompass exercise progress measurement related in some manner to a strap, belt or the like, as are reflected in U.S. Pat. No. 4,632,393 (1986) to Van Noord, entitled Multi-Purpose Exercising Apparatus, and U.S. Pat. No. 7,334,472 (2008) to Seo, entitled Apparatus and Method for Measuring Quantity of Physical Exercise Using Acceleration Sensor. Various forms of exercise, e.g., aerobics exercise, have been the subject of particular efforts to quantify and/or display the effect of such exercise. Such are reflected in EP Patents EP1074279A1 and EP19990917188, which are related applications.

Various body mass index calculators exist by which reduction of the ratio of fat to body mass may be measured and displayed, as is reflected in U.S. Design Pat. No. D536,030S (2007) to Wolff, entitled Body Mass Index Calculator.

Notwithstanding the above, the most related art known to the within inventors appears on Internet sites, particularly including the MyoTape Body Tape Measure, produced by Accu Measure (see www.portablesupplements.com/myotape.asp) which offers a number of body measurement devices, some of mechanical nature but most electronic. These include the above-referenced MyoTape Body Tape Measure, a Myo-Body Tools product, the MyoTape D electronic version of the MyoTape Body Tape Measure, and various tricep straps, ab straps, yogi straps, stretch straps and other straps. None of these however include any form of tape measure or the like incorporated therein, nor do any suggest any mode of use thereof by which an otherwise visible measurement can be selectably precluded from observation. Web pages of this type also appear in the exercise strap and exercise product departments of amazon.com and target.com.

It is therefore to be appreciated that the prior art has not addressed, and thereby has not attempted to solve the issues and objects addressed of the present invention, as set forth below.

SUMMARY OF THE INVENTION

A belt or band-like exercise result measurement article with selectable display aspect comprising a planar strip of substantially flexible material having a longitudinal axis, first and second ends, an inner surface having properties of adherence to skin or clothing of a user of said article, and an outer surface formed of loop, VELCRO-like or hook engagable material, said outer surface further having, substantially along an entire longitudinal length thereof, at least one linear scale imprinted upon said surface and parallel to said axis of said planar strip; a buckle having one element thereof secured to said first end of said strip; a first segment of a hook material affixed to said inner surface, proximally to said second end of said strip and press-fittably securable to said outer surface and proximally to said first end of said strip, in which upon positioning through said buckle, of said second end of said strip of said article, an opposite element of said buckle will define a measurement of scale corresponding to a circumference dimension of a waist or other body part about which said strip is secured; and a second segment of a hook material affixed to said loop or hook-engagable outer surface of said strip, proximally to said second end of said strip, enabling positioning of said second end of said strip through said buckle permitting engagement of said first hook segment in securable contact with said loop or hook-engagable material of said outer surface, thereby precluding from view that point upon said outer surface that would otherwise display said dimension of said waist or other body part about which the instant article is applied.

It is an object of the invention to provide an article to furnish selectable display, upon a belt, band, or the like of exercise-result progress or of the natural physique of the user.

It is a further object to furnish a simple to use, and economic to manufacture, article of the above type.

It is a still further object to provide such an article useful upon various body parts inclusive of the waist.

It is another object to provide a belt or band-like article of the above type that may be used for promotional purposes.

It is still another object to furnish such an article having utility in weight loss.

The above and yet other objects and advantages of the present invention will become apparent from the hereinafter set forth Brief Description of the Drawings, Detailed Description of the Invention, and Claims appended herewith.

DETAILED DESCRIPTION OF THE INVENTION

Figure 1:
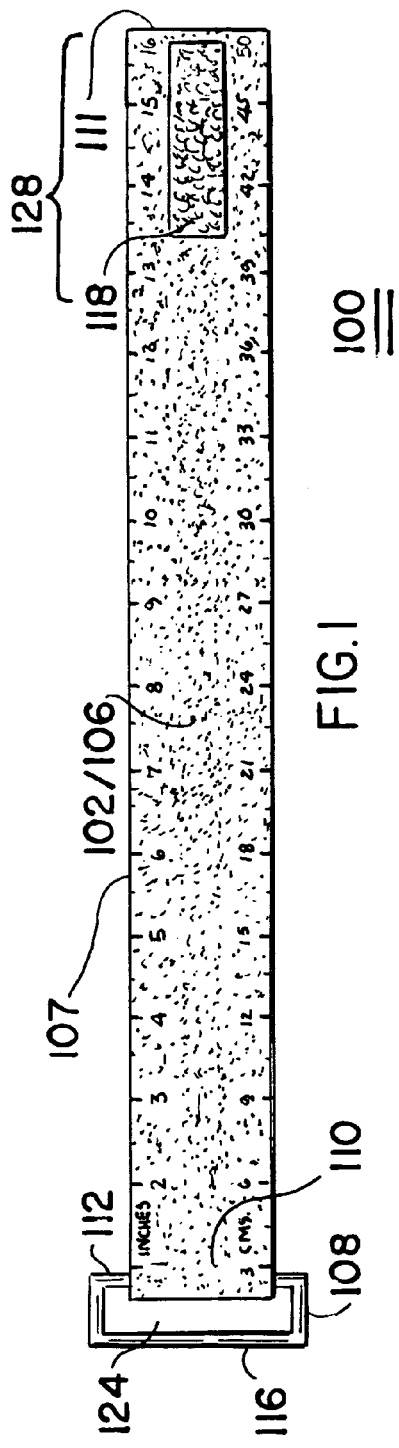
FIG. 1 is a front elevational view of a first embodiment of the inventive article.
Figure 2:
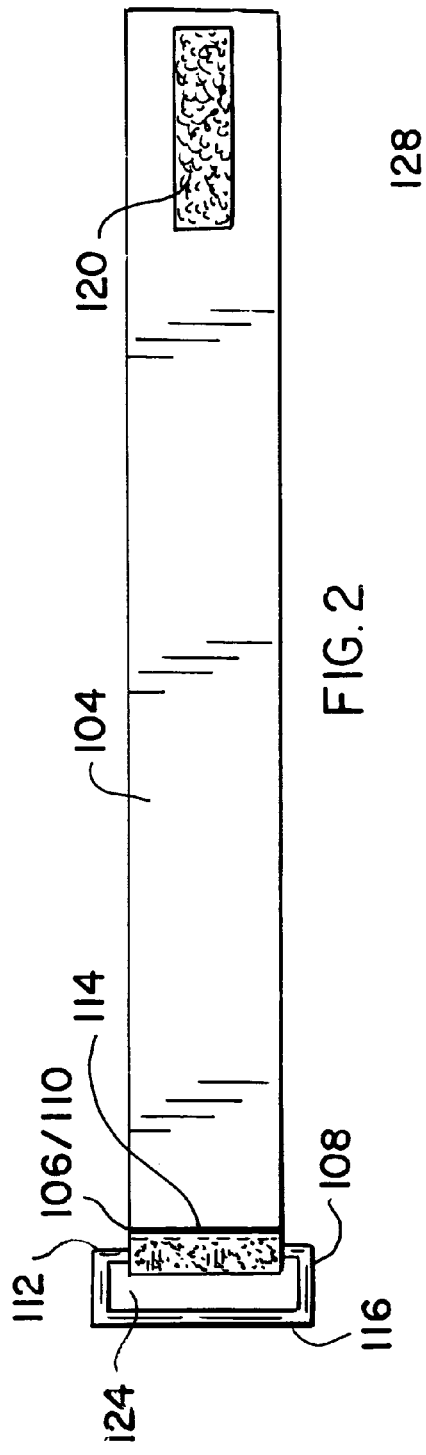
FIG. 2 is a rear elevational view thereof.
Figure 3:
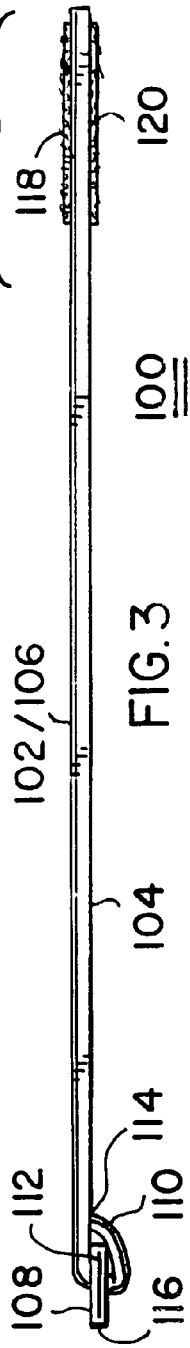
FIG. 3 is a top plan edge view of the article shown in FIGS. 1 and 2.

With reference to the front elevational view of FIG. 1, the present inventive belt-like exercise result measurement and display article 100 may be seen to comprise a flexible strip 102 of material having an inner surface 104 (see FIG. 2) and an outer surface 106 (see FIGS. 1 and 3). Said inner surface 104 is typically a flexible or rubber-like material having properties of adherence to both human skin and clothing that it is placed into frictional contact therewith, or is stable when placed thereagainst. The outer surface 106 is a loop material. This flexible two face material is commercially available, and is commonly referred to as an elastomeric-fabric faced material. Suitable examples are VELSTRETCH Broad loop, MEDFLEX Brand loop, and VELCRO Brand RF provided by FASTENation, Inc., Clifton, N.J. Both of these provide a soft back surface and a durable loop surface. Furthermore, printing can be made on the loop surface. The outer face 106 is complementary to hook material and can be fastened to a hook material via a hook-loop connection mechanism, as known in VELCRO® tapes, or the like.

In FIG. 1 is also shown essential printing upon outer surface 106 which is applicable to the present invention. That is, there is printed an ascending scale, in the nature of a tape measure, from lower to higher values in both the English (Imperial) system 107 and the metric system 109. These scales are linear and are co-parallel with a longitudinal axis of article 100. As may be noted in FIGS. 1-3, article 100 is provided with a buckle 108, preferably having a solid rectangular geometry in which first end 110 of strip 102 is looped about a first major base or element 112 of the buckle 108 and is preferably secured to inner surface 104 of strip 106, preferably by stitching 114 which is schematically shown in FIGS. 2 and 3.

In the above mechanical system, the zero point for both the English and metric scales is preferably established by second major base or opposite element 116 of buckle 108 such that the about one inch or about 2.5 centimeter point of the respective scales 107 and 109 appear slightly to the right of first major base or element 112 of buckle 108, as is shown at the left in FIG. 1.

To the right of FIGS. 1-3 are shown respective first or inner hook segment 120 affixed on inner surface 104 and second or outer hook segment 118 affixed on an outer surface 106, the functions of which are set forth below. Both segments 118/120 are located within distal portion 128 of the article.

Figure 4:
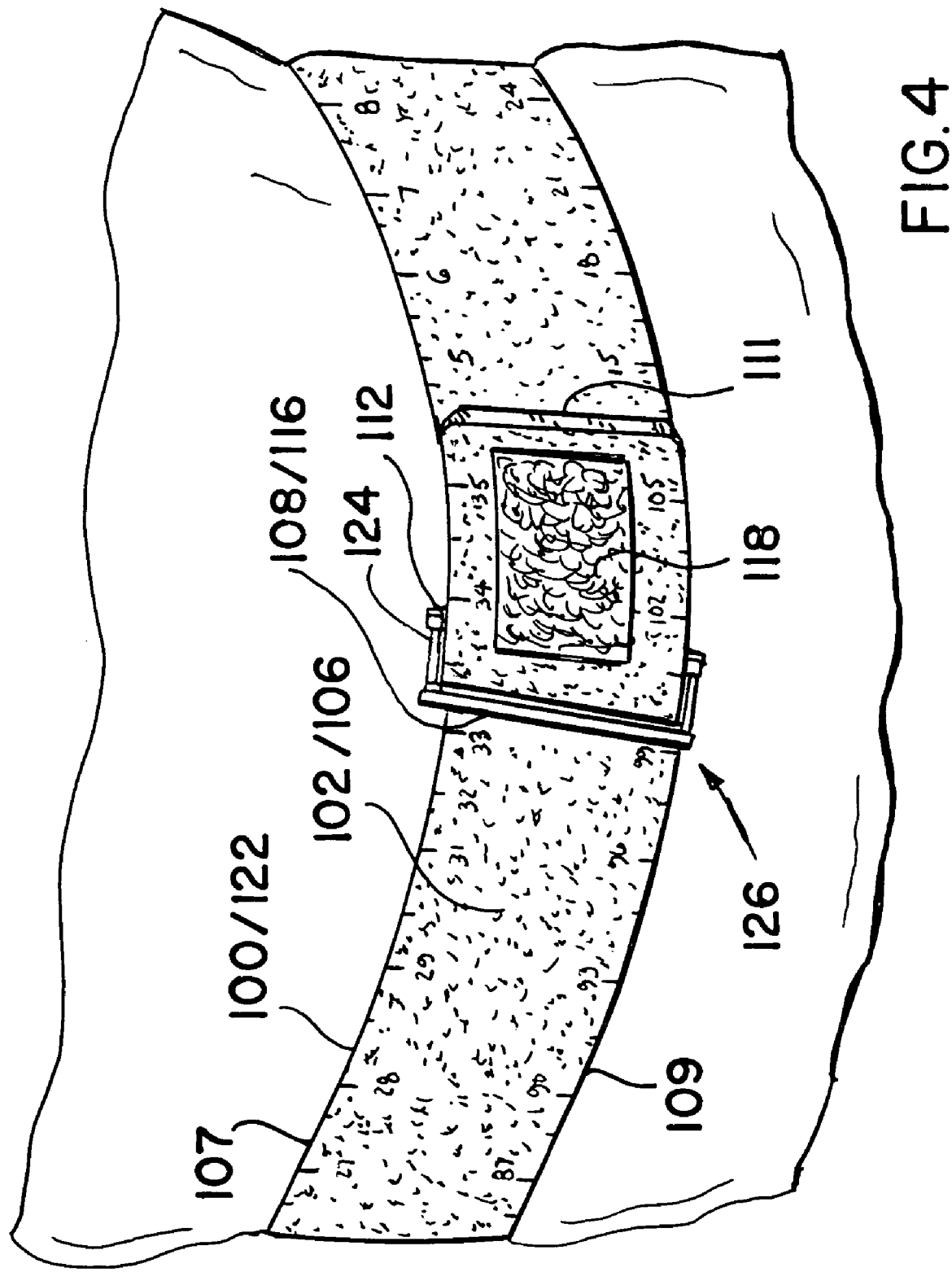
FIG. 4 is an operational view showing the use of the inventive article upon the waist of a user in which the display of the parameter of measurement of the waist is visible.
Figure 5:
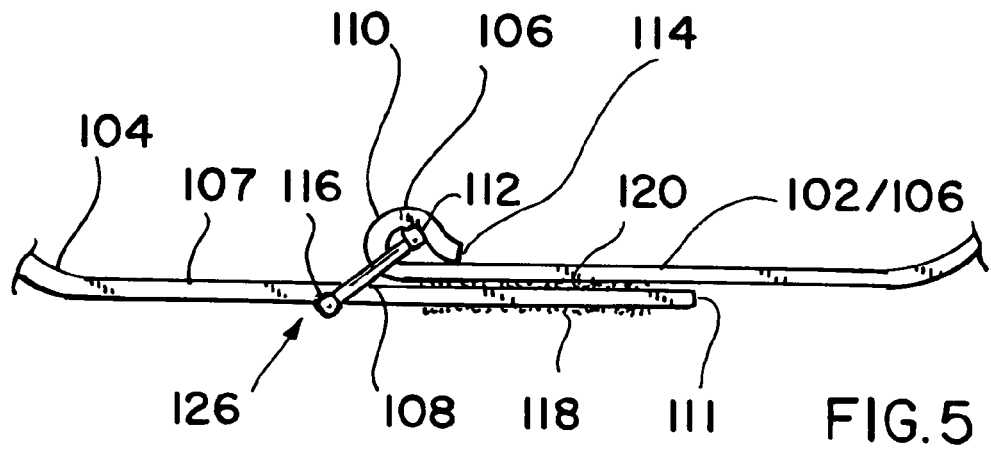
FIG. 5 is a top plan front fragmentary view of the view of FIG. 4.

As may be noted in the operational views of FIGS. 4-5, article 100 is therein shown secured about a waist 122 of a user thereof. Therein, second strip end 111 has passed through a buckle opening 124 and inner hook segment 120 is fixed in place in portion 128 proximally to first end 110 of strip 102 of article 100. Thereby, at point 126, there exists an exact circumference of the waist, when considering the width of the buckle, meaning that the measurement thereof, in both English and metric terms may thereby be observed immediately to the left of the second major rectangular base element 116 of buckle 108. This constitutes the so-called display mode of the invention and is intended to give the user the opportunity to display the extent of his or her exercise and/or dieting progress or normal enviable physique.

FIG. 5 is a top axial plan view of the inventive article when engaged upon the waist of the user in the manner shown in FIG. 4. Therein may be seen that inner hook segment 120 affixed on inner surface 104 of strip 102 of the article will engage the loop or hook engagable surface of outer surface 106, thereby (as above noted) permitting second major base 116 of buckle 108 to display one's waste measurement in both English and metric terms at point 126 of the article. Also shown in FIG. 5 is first end 110 and second end 111 of strip 102.

Figure 7:
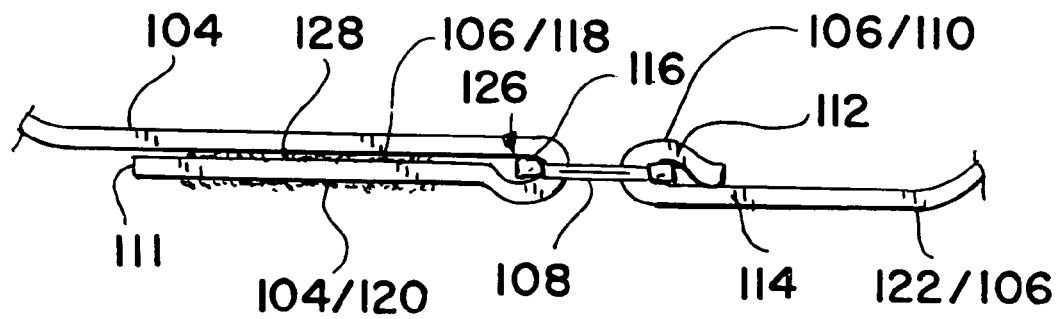
FIG. 7 is a top plan front fragmentary view of the view of FIG. 6.

In the event that the user does not wish to display his or her waist line (for whatever reason), distal portion 128 (see FIGS. 6-7) of strip 102 may be folded upon itself such that outer hook segment 118 engages outer surface 106, that is, the loop surface of strip 102. In this mode, point 126 of outer surface 106 is not visible, thus rendering it impossible for anyone to see the measurement of the waistline of the user.

Figure 6:
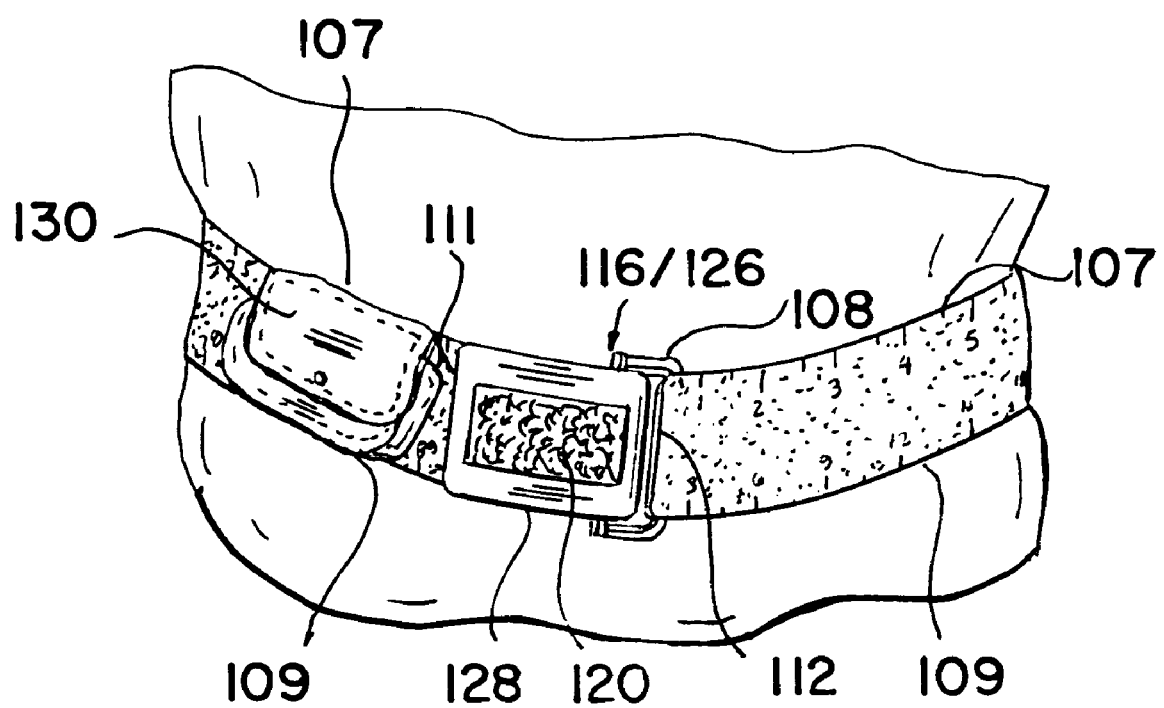
FIG. 6 is a view, similar to that of FIG. 4, however showing the use of the invention is a second mode in which the parameter of measurement of the waist of the user is hidden.

In FIG. 6 is also shown the use of article 100 with the addition of a pouch 130 within which may be held keys, credit cards, money and other such items of the user.

Figure 10:
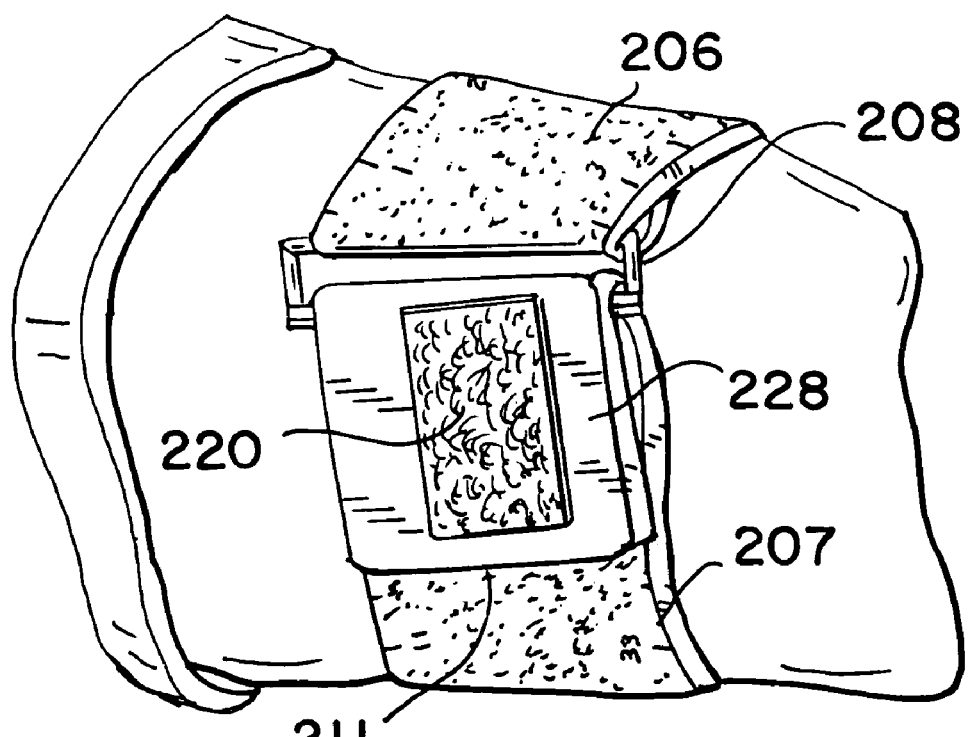
FIG. 10 is an operational view of a second mode of use of the second embodiment of the invention.
Figure 8:
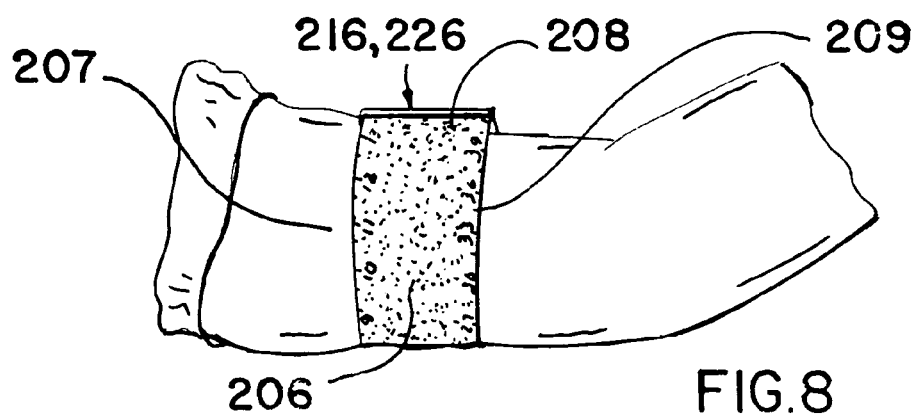
FIG. 8 is a view of a second embodiment of the invention, adapted for use with the bicep of calf, comparable to the view of FIG. 4 relative to the first embodiment, in which the dimensional parameters of the scales thereof are visible.
Figure 9:
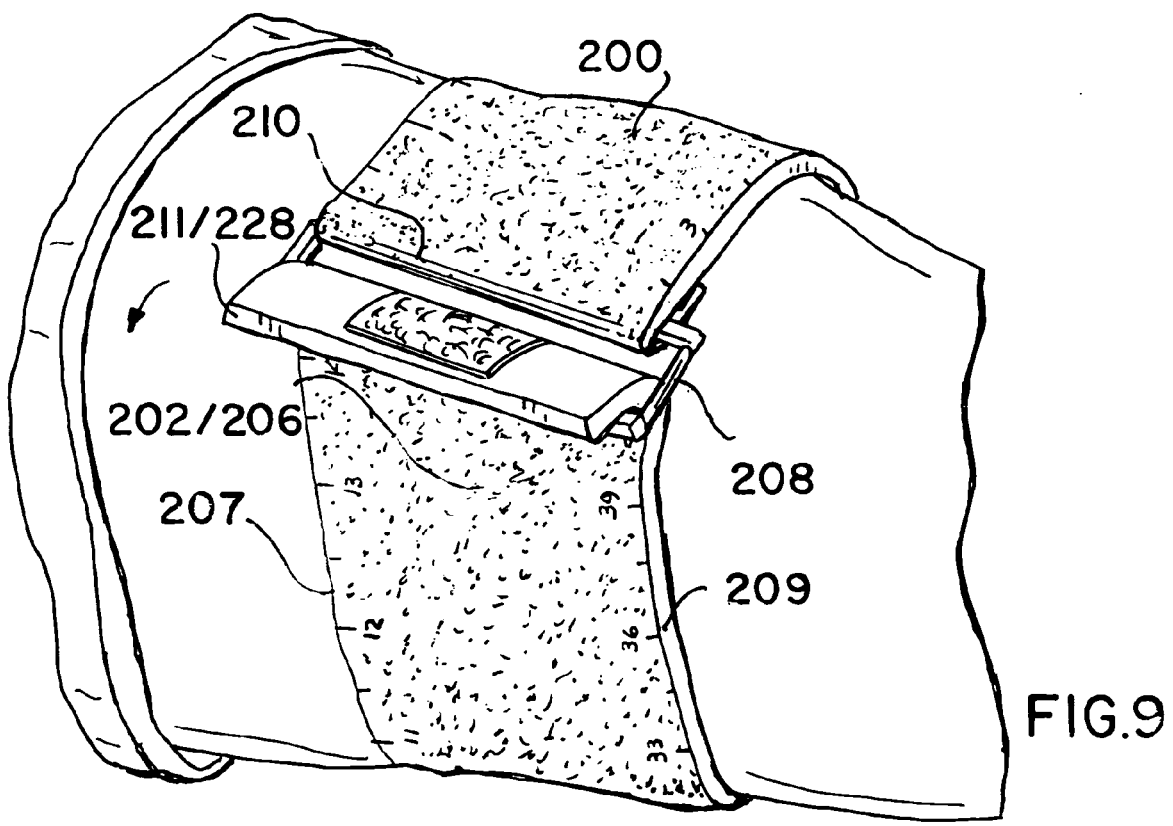
FIG. 9 is a transitional view showing the change in use of the embodiment of FIG. 7 from that of one in which the parameter of measurement is visible to that in which the parameter of measurement is not visible, namely, that as shown in FIG. 10.

In FIGS. 8-10 are shown another embodiment of the invention in which an article 200 is smaller in length and width and, thereby, may be used upon an upper arm or calf of the user in a manner substantially the same as above described with regard to the embodiment of FIGS. 1-7. Therein, all parts above-referenced correspond, namely, strip 202, first end 210, second end 211 (see FIG. 10), buckle 208 and the two modes of use thereof, namely, display mode and non-display mode. In FIG. 8 is shown article 200 in display mode. Therein, major base element 216 of the buckle 208 is the exact point of measurement 226 upon the English and metric scales 207 and 209 respectively. FIG. 9 shows a transition from display mode to non-display mode in which end 211 of article 200 passes through buckle 208 and therefrom is bent back upon itself in a similar manner to that shown in FIGS. 6-7 relative to article 100. The result of this process is shown in FIG. 10 which, thereby, corresponds to the non-display mode in regard to article 100.

It is to be appreciated that the loop material of outer surface 106 is available in a wide variety of colors and that such materials is also suitable to the printing thereon of any of a number of graphics, logos, trademarks, phrases, or the like, if one wishes. Also, accessories other than that of pouch 130 may be used in association with either embodiment of the present invention. Further, in a preferred embodiment, the flexible material of inner surface 104 is hydrophobic, or poor in absorbing moisture, which will maximize sweating of the waist, particularly of adipose tissue associated with the waistline.

The present invention represents a simple to manufacture product that can be marketed at a reasonable price sufficient to be of interest to the mass market of fitness conscious people of every type.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What we claim is:

1. A belt or band-like exercise result measurement article with selectable display and non-display modes, the article comprising:

(a) a planar strip of a flexible material having a longitudinal axis, first and second ends, an inner surface having properties of adherence to skin or clothing of a user of said article, and an outer surface formed of a loop or hook-engagable material, said outer surface further having, substantially along an entire longitudinal length thereof, at least one linear scale imprinted upon said surface and parallel to said axis of said planar strip;

(b) a buckle having one base thereof affixed to said first end of said strip and an opposing unfixed base;

(c) a first segment of a hook material affixed to said inner surface, proximally to said second end of said strip; and (d) a second segment of a hook material affixed to said loop material of said outer surface of said strip, opposing said first segment of a hook material;

wherein at said display mode, said second end of said strip is passed through said buckle with said first segment of the hook material attached to said outer surface of said strip and said second segment of the hook material remaining unattached, thereby said opposing unfixed base of said buckle being pressed on said outer surface against a point on said linear scale, said point being visible and displaying a parameter of measurement corresponding to a circumference dimension of a waist or other body part about which said strip is secured; while at said non-display mode, said second end of the strip is passed through said buckle and folded back against said unfixed base of said buckle, with said second segment of the hook material attached to said outer surface of said strip and said first segment of the hook material remaining unattached, thereby said point of said linear scale pressed on by said unfixed base of said buckle being covered by folded portion of said strip, and said parameter of measurement being hidden.

2. The article as recited in claim 1, in which said linear scale comprises a tape measure imprinted along a longitudinal axis of said strip, said scale ascending in dimensional parameter from said buckle.

3. The article as recited in claim 1, in which said at least one linear scale comprises two linear scales, one each imprinted along an opposite longitudinal edge of said strip on said outer surface thereof, one of said scales defining English or Imperial units, and another of said scales defining metric units, each of said scales ascending in dimensional parameter from said buckle.

4. The article as recited in claim 3, in which said inner surface comprises a flexible material.

5. The article as recited in claim 4, in which said inner surface defines properties that included sweating to tissue in contact therewith.

6. The article as recited in claim 4, in which said outer surface comprises a cloth-like material available in a variety of colors in which printing thereon of any graphic, name, trademark slogan, or the like may be effected.

7. The article as recited in claim 3, in which a total length of said strip approximates the waistline of a user.

8. The article as recited in claim 3, in which a total length of said strip approximates the prospective circumference of a bicep and tricep of a user.

9. The article as recited in claim 3, in which a total length of said strip approximates, the prospective circumference of a calf of a user.

10. The article as recited in claim 3, in which a total length of said strip approximates the neck of a user.

* * * * *